(12) United States Patent
Ben Moha-Lerman et al.

(10) Patent No.: US 8,283,487 B2
(45) Date of Patent: Oct. 9, 2012

(54) PROCESSES FOR THE PREPARATION AND PURIFICATION OF GABAPENTIN ENACARBIL

(75) Inventors: Elena Ben Moha-Lerman, Kiryat Ono (IL); Tamar Nidam, Yehud (IL); Meital Cohen, Petach-Tikva (IL); Sharon Avhar-Maydan, Givataym (IL); Anna Balanov, Rehovot (IL)

(73) Assignee: Teva Pharmaceutical Industries Ltd., Petach-Tikva (IL)

( * ) Notice: Subject to any disclaimer, the term of this patent is extended or adjusted under 35 U.S.C. 154(b) by 249 days.

(21) Appl. No.: 12/626,682

(22) Filed: Nov. 26, 2009

(65) Prior Publication Data

US 2010/0160665 A1 Jun. 24, 2010

Related U.S. Application Data

(60) Provisional application No. 61/118,265, filed on Nov. 26, 2008, provisional application No. 61/208,565, filed on Feb. 24, 2009, provisional application No. 61/180,265, filed on May 21, 2009, provisional application No. 61/240,793, filed on Sep. 9, 2009.

(51) Int. Cl.
*C07C 271/16* (2006.01)
(52) U.S. Cl. ........................................ 560/115
(58) Field of Classification Search .............. None
See application file for complete search history.

(56) References Cited

U.S. PATENT DOCUMENTS

| | | | |
|---|---|---|---|
| 4,760,057 A | 7/1988 | Alexander | |
| 6,255,526 B1 | 7/2001 | Pesachovich et al. | |
| 6,818,787 B2 | 11/2004 | Gallop et al. | |
| 7,227,028 B2 | 6/2007 | Gallop et al. | |
| 7,232,924 B2 | 6/2007 | Raillard et al. | |
| 2003/0176398 A1 | 9/2003 | Gallop et al. | |
| 2004/0077553 A1* | 4/2004 | Gallop et al. | 514/19 |
| 2005/0154057 A1 | 7/2005 | Estrada et al. | |
| 2007/0049627 A1 | 3/2007 | Tran | |

FOREIGN PATENT DOCUMENTS

| | | |
|---|---|---|
| WO | WO 02/100347 | 12/2002 |
| WO | WO 2005/037784 | 4/2005 |

OTHER PUBLICATIONS

X. Yuan et al. "In Situ Preparation of Zinc Salts of Unsaturated Carboxylic Acids to Reinforce NBR" J. Applied Polymer Science, vol. 77, p. 2740-2748 (2000).
J. Alexander et al. "(Acyloxy)alkyl Carbamates as Novel Bioreversible Prodrugs for Amines: Increased Permeation through Biological Membranes" *J. Med. Chem.* 1988, 31, pp. 318-322.
S.M. Rahmathullah et al. "Prodrugs for Amidines: Synthesis and Anti-Pneumocystis carinii Activity of Carbamates of 2,5-Bis(4-amidinophenyl)furan" *J. Med. Chem.* 1999, 42, pp. 3994-4000.

* cited by examiner

*Primary Examiner* — Joseph K. McKane
*Assistant Examiner* — Alicia L Otton
(74) *Attorney, Agent, or Firm* — Arent Fox LLP

(57) ABSTRACT

Gabapentin enacarbil was prepared and purified from intermediates such as 1-haloalkyl carbamate or carbonate and diacid acetal skeleton. For example, a 1-haloalkyl carbonate or carbamate was prepared by combining a $C_1$ to $C_{10}$ alcohol or $C_1$ to $C_{10}$ primary amine, a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloalkyl haloformate of the following formula:

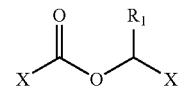

wherein each X is independently selected from Br, I, or Cl; $R_1$ is alkyl or H; and a $C_6$ to $C_{21}$ tertiary amine.

20 Claims, No Drawings

PROCESSES FOR THE PREPARATION AND PURIFICATION OF GABAPENTIN ENACARBIL

CROSS-REFERENCE TO RELATED APPLICATIONS

This application claims the benefit of U.S. Provisional Patent Application Ser. Nos. 61/118,265, filed Nov. 26, 2008; 61/208,565, filed Feb. 24, 2009; 61/180,265, filed May 21, 2009; and 61/240,793, filed Sep. 9, 2009, which are incorporated herein by reference.

FIELD OF THE INVENTION

The present invention relates to the preparation of 1-haloalkyl carbamate or carbonate and diacid acetal skeleton, intermediates in the preparation of gabapentin enacarbil, as well as processes for preparing and purifying gabapentin enacarbil.

BACKGROUND OF THE INVENTION

Gabapentin ("GBP"), 1-(aminomethyl)cyclohexaneacetic acid is described according to the following formula:

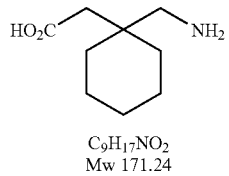

$C_9H_{17}NO_2$
Mw 171.24

GBP is a white to off-white crystalline solid with a pKa1 of 3.7 and a pKa2 of 10.7. GBP is marketed by Pfizer under the trade name Neurontin®.

GBP is used in the treatment of cerebral diseases such as epilepsy. In animal models of analgesia, GBP prevents allodynia (pain-related behavior in response to a normally innocuous stimulus) and hyperalgesia (exaggerated response to painful stimuli). GBP also decreases pain related responses after peripheral inflammation. Animal test systems designed to detect anticonvulsant activity, proved that GBP prevents seizures as do other marketed anticonvulsants.

Gabapentin enacarbil ("GBPE"), 1-{[(α-isobutanoyloxyethoxy)carbonyl]-aminomethyl}-1-cyclohexane acetic acid, is a transported prodrug of GBP and is described according to the following formula:

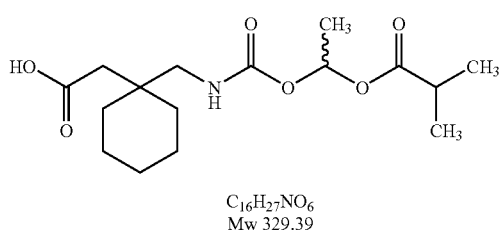

$C_{16}H_{27}NO_6$
Mw 329.39

GBPE was developed to improve some of the bioavailability limitations that are known in GBP. GBPE is recognized by high-capacity transport proteins expressed all along the intestinal tract, making it suitable for sustained-release formulation for colonic absorption. After its absorption in the blood, GBPE is rapidly converted to GBP.

A coupling process of 1-haloalkyl carbamates or carbonates with carboxylic acid is used in synthetic chemistry and particularly in medicinal chemistry, as exemplified in *J. Med. Chem.* 1999, 42, pages 3994-4000 and *J. Med. Chem.* 1988, 31, pages 318-322, as a way to construct the diacid-acetal skeleton. The process is described in scheme 1 below:

Scheme 1

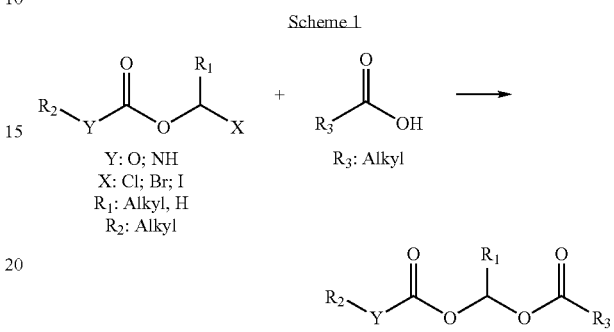

Y: O; NH
X: Cl; Br; I
$R_1$: Alkyl, H
$R_2$: Alkyl
$R_3$: Alkyl

The use of a coupling agent in the process depicted above is known in the art with the use of coupling agents such as mercury acetate, mercury oxide and silver oxide. This is exemplified in U.S. Pat. No. 6,818,787 ("the '787 patent"). The '787 patent describes a process for preparing GBPE according to scheme 1 using silver oxide (Ag$_2$O) as a coupling agent. The process for preparing compound 18 from compound 16 described in the '787 patent and illustrated in scheme 2 below is a two step process, where compound 17 is prepared separately.

Scheme 2

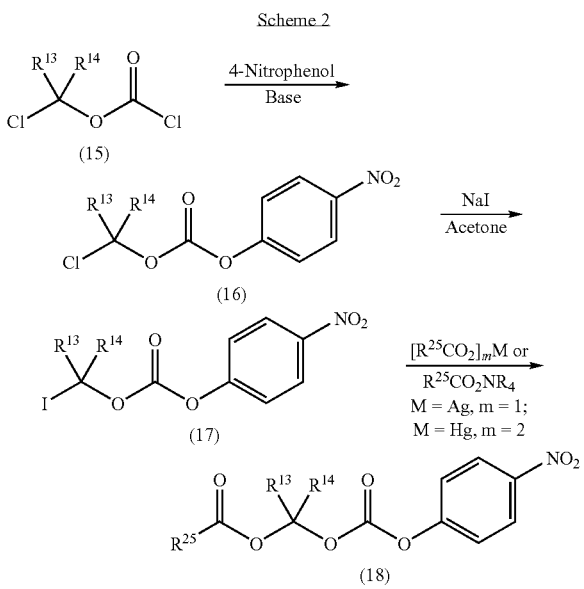

GBPE and processes for its preparation are described in U.S. Pat. Nos. 6,818,787, 7,232,924 and 7,227,028, which are incorporated herein by reference.

Like any synthetic compound, gabapentin enacarbil can contain extraneous compounds or impurities. These impurities may include unreacted starting materials, by-products of the reaction, products of side reactions, and/or degradation products.

Impurities in gabapentin enacarbil or any active pharmaceutical ingredient ("API") are undesirable and, in extreme cases, might be harmful to a patient being treated with a dosage form of the API.

There is a need in the art for an improved process for preparing GBPE and its intermediates, and processes for purifying GBPE.

SUMMARY OF THE INVENTION

The present invention encompasses a process for preparing 1-haloalkyl carbonate or carbamate comprising: combining $C_1$ to $C_{10}$ alcohol or $C_1$ to $C_{10}$ primary amine, a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloalkyl haloformate of the following formula:

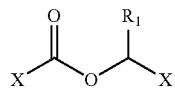

wherein each X is independently selected from Br, I, or Cl; $R_1$ is alkyl or H; and a $C_6$ to $C_{21}$ tertiary amine.

In another embodiment, the present invention encompasses a process for preparing 1-chloroethyl 4-nitrophenyl carbonate ("CEC-NP") comprising: combining 4-nitrophenol, toluene, 1-chloroethyl chloroformate and a tertiary amine selected from the group consisting of: tributyl amine ("TBA") and triethyl amine ("TEA").

In yet another embodiment, the present invention encompasses a process for preparing GBPE comprising preparing 1-haloalkyl carbonate or carbamate and further converting it to GBPE.

In one embodiment, the present invention encompasses a process for preparing diacid acetal skeleton having the following structure:

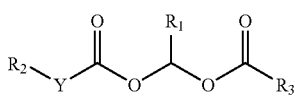

wherein Y is O or NH, $R_1$ is alkyl or H, $R_3$ is alkyl and $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', _N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl comprising: combining a carboxylic acid with 1-haloalkyl carbamates or carbonates in the presence of a coupling agent selected from the group consisting of Cu(OAc)$_2$, Zn(OAc)$_2$, Cu$_2$O, CuO, CeO$_2$, NiO, ZnO and Cu(O$_2$CCHMe$_2$)$_2$.

In another embodiment, the present invention encompasses a process for preparing 1-(isobutyryloxy)ethyl 4-nitrophenyl carbonate ("AEC-NP") comprising: combining CEC-NP with isobutyric acid in the presence of zinc oxide.

In another embodiment, the present invention encompasses a one-pot process for preparing diacid acetal skeleton comprising: combining a $C_1$ to $C_{10}$ alcohol or $C_1$ to $C_{10}$ primary amine; a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloalkyl haloformate of the following formula:

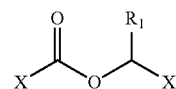

wherein each X is independently selected from Br, I, or Cl and $R_1$ is alkyl or H; and a $C_6$ to $C_{21}$ tertiary amine to obtain a reaction mixture; and adding carboxylic acid to the reaction mixture in the presence of a coupling agent selected from the group consisting of Cu(OAc)$_2$, Zn(OAc)$_2$, Cu$_2$O, CuO, CeO$_2$, NiO, ZnO and Cu(O$_2$CCHMe$_2$)$_2$.

In another embodiment, the present invention further encompasses a process for preparing AEC-NP comprising: combining 4-nitrophenol with toluene, 1-chloroethyl chloroformate, a base selected from the group consisting of TEA and TBA; and adding isobutyric acid in the presence of a coupling agent, such as ZnO.

In another embodiment, the present invention encompasses a process for preparing GBPE comprising preparing 1-(isobutyryloxy)ethyl 4-nitrophenyl carbonate ("AEC-NP") and further converting it to GBPE.

In yet another embodiment, the present invention encompasses a process for preparing GBPE comprising: preparing 1-(isobutyryloxy)ethyl 4-nitrophenyl carbonate ("AEC-NP") according to the process above and further converting it to GBPE.

In one embodiment, the present invention further encompasses a process for preparing gabapentin enacarbil comprising: combining gabapentin with a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a base selected from a group consisting of: $C_6$ to $C_{21}$ tertiary amine, $K_2CO_3$, $KHCO_3$, $Na_2CO_3$ and $NaHCO_3$; and AEC-NP.

In one embodiment, the present invention encompasses a purification process of GBPE comprising reducing the NP and NP derivatives in GBPE, followed by acidic extractions.

In another embodiment, the present invention encompasses a process comprising: combining GBPE containing NP and/or NP derivatives with a polar solvent or an aromatic solvent to obtain a solution, adding gaseous $H_2$ or formic acid salt in the presence of Pd/C or Pt/C to the solution; and extracting with an acid to obtain GBPE.

In yet another embodiment, the present invention encompasses a process comprising: dissolving GBPE containing NP and/or NP derivatives in $C_1$-$C_4$ carboxylic acid or HCl to obtain a solution; adding a metal selected from the group consisting of: iron, zinc and magnesium to the solution; and extracting with acid.

In yet another embodiment, the present invention encompasses a process comprising: loading GBPE on a column filled with cross-linked dextran gel in toluene; and eluting GBPE with toluene or a toluene/hexane solution to obtain GBPE.

In one embodiment, the present invention encompasses a one-pot process for preparing GBPE comprising: combining $C_1$ to $C_{10}$ alcohol or $C_1$ to $C_{10}$ primary amine; a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloethyl haloformate of the following formula:

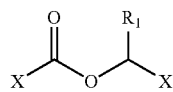

wherein X is independently selected from Br, I, or Cl and $R_1$ is methyl; and a $C_6$ to $C_{21}$ tertiary amine; adding isobutyric acid in the presence of a coupling agent selected from the group consisting of $Cu(OAc)_2$, $Cd(OAc)_2$, $Zn(OAc)_2$, $Cu_2O$, CuO, $CeO_2$, CdO, NiO, ZnO and $Cu(O_2CCHMe_2)_2$; adding gabapentin and a base selected from a group consisting of: $C_6$ to $C_{21}$ tertiary amine, $K_2CO_3$, $KHCO_3$, $Na_2CO_3$ and $NaHCO_3$ to obtain GBPE; reducing the GBPE, followed by acidic extraction, concentrating the solvent and adding hexane, heptane or a solution of heptane and EtOAc to obtain a precipitate.

In another embodiment, the present invention further encompasses a one-pot process for preparing GBPE comprising: combining 4-nitrophenol, toluene, 1-chloroethyl chloroformate and a base selected from the group consisting of TEA and TBA; adding isobutyric acid in the presence of ZnO; adding GBP and a base selected from the group consisting of TEA and $K_2CO_3$; adding potassium formate in the presence of palladium over carbon; and adding hexane, heptane or heptane/EtOAc.

DETAILED DESCRIPTION OF THE INVENTION

As used herein, the term "1-haloalkyl carbamate or carbonate" refers to a compound having the following formula:

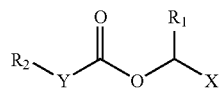

wherein Y is O or NH, X is independently selected from Cl, Br, or I, $R_1$ is alkyl or H, and $R_2$ is alkyl or a substituted aromatic hydrocarbon. Preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', —N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a moiety selected from the group consisting of: —NO$_2$, —S(O)$_2$O—, —S(O)$_2$OH and —S(O)$_2$R', most preferably, $R_2$ is p-nitrophenyl. Preferably, Y is O and $R_1$ is a linear alkyl.

As used herein, the term "alkyl" refers to saturated or unsaturated, straight or branched hydrocarbon chain or cyclic monovalent hydrocarbon radical consisting of carbon and hydrogen atoms, having from 1 to 6 carbon atoms, and which is attached to the rest of the molecule by a single bond. Examples of alkyl groups include, but are not limited to, methyl, ethyl, n-propyl, isopropyl, n-butyl, t-butyl, and isobutyl. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds.

As used herein, the term "one-pot" refers to a process done without isolating the process intermediates from the reaction solvent or mixture.

As used herein, the term "carboxylic acid" refers to a compound having the following formula:

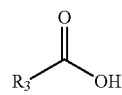

wherein $R_3$ is alkyl. Preferably, $R_3$ is selected from the group consisting of methyl, ethyl and isopropyl. Preferably, the carboxylic acid is isobutyric acid.

As used herein, the term "CEC-NP" refers to 1-chloroethyl 4-nitrophenyl carbonate having the following structure:

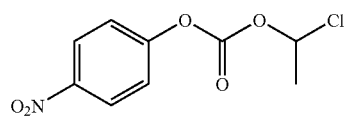

As used herein, the term "AEC-NP" refers to 1-(isobutyryloxy)ethyl 4-nitrophenyl carbonate having the following structure:

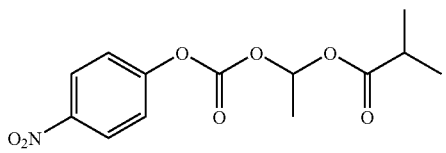

As used herein, the term "NP" refers to nitrophenol.

As used herein, the term "room temperature" refers to a temperature of about 15° C. to about 30° C., preferably, about 20° C. to about 25° C.

As used herein, the term "reduced pressure" refers to a pressure less than atmospheric pressure, more preferably, of about 10 mbar to about 50 mbar.

As used herein, the term "protected gabapentin" refers to gabapentin possessing a protecting group on its carboxylic moiety, preventing gabapentin from acting as a nucleophile. Suitable protecting groups are well known in the art.

As used herein, the term "substantially pure GPBE" refers to GBPE having an assay of about 95% or more, measured versus its standard. Preferably, "substantially pure GBPE" has an assay of about 97% or more, more preferably, of about 99% or more, even more preferably, of about 99.3% or more, most preferably, of about 99.8% or more.

As used herein, the term "GBPE-mix" refers to a nearly equimolar mixture of GBPE and NP and/or NP derivatives.

As used herein, the term "HPLC" refers to High-performance liquid chromatography.

As used herein, the term "NP derivatives" refers to chemical structures containing a nitrophenol moiety. The term "NP derivatives" includes, for example, CEC-NP and AEC-NP.

As used herein, the term "% area by HPLC" refers to the area in an HPLC chromatogram of one or more peaks compared to the total area of all peaks in the HPLC chromatogram expressed in percent of the total area.

The present invention refers to a process for preparing 1-haloalkyl carbonate or carbamate, such as CEC-NP, preferably avoiding the use of solvents such as tetrahydrofuran ("THF") and chloroform which are used in the prior art. THF is expensive and might form peroxides in the presence of oxygen, which are explosive. Chloroform is a toxic solvent which is not recommended as well. Preferred processes of the invention use a recoverable base which makes the process environmentally friendly, and improves the cost efficiency of the process compared to the prior art; the use of TEA and THF together, as described in the prior art, prevents the base from being recovered. The combination of toluene and TEA used according to preferred embodiments of the present invention allows easier separation of TEA*HCl formed during the process, by filtration. Such a procedure has economic and environmental advantages, since the isolated TEA*HCl can be recovered.

The present invention encompasses a process for preparing 1-haloalkyl carbonate or carbamate comprising: combining $C_1$ to $C_{10}$ alcohol or $C_1$ to $C_{10}$ primary amine, a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloalkyl haloformate of the following formula:

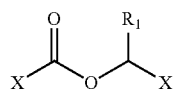

wherein each X is independently selected from Br, I, or Cl; $R_1$ is alkyl or H; and a $C_6$ to $C_{21}$ tertiary amine.

Preferably, the $C_{1-10}$ alcohol has the formula $R_2$—Y—H wherein Y is O, and the $C_{1-10}$ primary amine has the formula $R_2$—$YH_2$ wherein Y is N.

Preferably, $R_2$ is alkyl or a substituted aromatic hydrocarbon. Preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', —N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a group selected from the group consisting of: —NO$_2$, —S(O)$_2$O—, —S(O)$_2$OH and —S(O)$_2$R', most preferably, $R_2$ is p-nitrophenyl.

Preferably, the 1-haloalkyl carbonate is CEC-NP.

Preferably, the process comprises dissolving $C_1$ to $C_{10}$ alcohol or $C_1$ to $C_{10}$ primary amine in a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof, followed by the addition of a $C_6$ to $C_{21}$ tertiary amine and 1-haloalkyl haloformate. Preferably, the $C_6$ to $C_{21}$ tertiary amine is a $C_6$ to $C_{12}$ tertiary amine, more preferably, TEA.

Typically, the $C_1$ to $C_{10}$ alcohol is a $C_6$ to $C_{10}$ aromatic alcohol, more preferably, phenol, more preferably, a substituted phenol, even more preferably, phenol substituted with a nitro group, most preferably, 4-nitrophenol. Preferably, the $C_1$ to $C_{10}$ primary amine is a $C_6$ to $C_{10}$ primary aromatic amine, more preferably, aniline.

Preferably, the solvent is toluene.

Optionally, the solution of the $C_{1-10}$ alcohol or $C_{1-10}$ primary amine in the solvent is cooled before the addition of the 1-haloalkyl haloformate and the $C_6$ to $C_{21}$ tertiary amine. Preferably, the cooling is to a temperature of about 15° C. to about 0° C., more preferably, to a temperature of about 10° C. to about 0° C., most preferably, to a temperature of about 5° C.

Preferably, the 1-haloalkyl haloformate is 1-chloroalkyl haloformate, more preferably, 1-chloroethyl chloroformate.

Preferably, the $C_6$ to $C_{21}$ tertiary amine is tributyl amine ("TBA") or triethyl amine ("TEA").

The use of TEA in a combination with toluene is advantageous as TEA.HCl can be removed by filtration without the need of extraction, and allows obtaining the 1-haloalkyl carbonate or carbamate more efficiently.

Preferably, $C_6$ to $C_{21}$ tertiary amine is added drop-wise, followed by the addition of 1-haloalkyl haloformate.

Preferably, following the addition of $C_6$ to $C_{21}$ tertiary amine, a mixing step (e.g., stirring, shaking, etc.) is performed. Preferably, the mixing is for about 30 minutes to about 10 hours. Preferably, the mixing is at a temperature of about 10° C. to about 100° C., more preferably, the mixing is at about room temperature.

Optionally, for example when TBA is used, the 1-haloalkyl carbonate or carbamate is isolated. Preferably, the isolation comprises: washing the solution with HCl, water and brine to obtain a two-phase system; separating the phases; and removing the solvent (e.g., toluene). The solvent can be removed by methods known in the art, such as evaporation.

The present invention encompasses a process for preparing CEC-NP comprising: combining 4-nitrophenol, solvent (preferably toluene), 1-chloroethyl chloroformate and a tertiary amine selected from the group consisting of: TBA and TEA.

The present invention also encompasses a process for preparing GBPE comprising: preparing 1-haloethyl carbonate or carbamate according to the process described above and further converting it to GBPE. The process parameters are, preferably, the same as those described above.

The present invention also encompasses a process for preparing GBPE comprising: preparing CEC-NP according to the process described above and further converting it to GBPE. The process parameters are, preferably, the same as those described above.

The present invention refers to a coupling process for preparing diacid acetal skeleton of 1-haloalkyl carbamate or carbonate with carboxylic acid, according to scheme 3 below:

Scheme 3

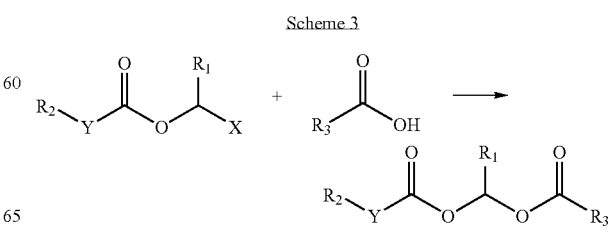

in the presence of new coupling agents, wherein Y is O or NH, X is independently selected from Cl, Br, or I, $R_1$ is alkyl or H, $R_3$ is alkyl and $R_2$ is alkyl or a substituted aromatic hydrocarbon. More preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', _N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a moiety selected from the group consisting of: —NO$_2$, —S(O)$_2$O—, —S(O)$_2$OH and —S(O)$_2$R'. Most preferably, $R_2$ is p-nitrophenyl.

Coupling agents used in the art include mercury acetate, mercury oxide and silver oxide. Such coupling agents possess several disadvantages, as these agents are expensive and thus increase the raw material costs of the final product. In addition, mercury is highly toxic. In the '787 patent, the carboxylic acid is added as silver isobutyrate, prepared separately. In contrast, preferred processes of the invention for the preparation of the diacid acetal skeleton from 1-haloalkyl carbonate or carbamate, such as the preparation of AEC-NP from CEC-NP, includes an in-situ formation of the zinc-carboxylate salt, thus making the process more efficient than that of the '787 patent. In addition, the yield of the preferred processes of the present invention is superior to that of the '787 process.

The present invention encompasses a process for preparing diacid acetal skeleton having the following structure:

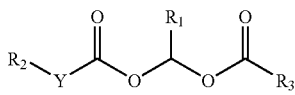

wherein Y is O or NH, $R_1$ is alkyl or H, $R_3$ is alkyl and $R_2$ is alkyl or a substituted aromatic hydrocarbon comprising: combining a carboxylic acid with 1-haloalkyl carbamates or carbonates in the presence of a coupling agent selected from the group consisting of Cu(OAc)$_2$, Zn(OAc)$_2$, Cu$_2$O, CuO, CeO$_2$, NiO, ZnO and Cu(O$_2$CCHMe$_2$)$_2$. The process is done according to scheme 3. Preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', _N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a moiety selected from the group consisting of: —NO$_2$, —S(O)$_2$O—, —S(O)$_2$OH and —S(O)$_2$R', most preferably, $R_2$ is p-nitrophenyl.

Preferably, the coupling agent is ZnO. Preferably, the amount of the coupling agent is about 1 equivalent.

Preferably, the diacid acetal skeleton is AEC-NP.

Preferably, the carboxylic acid used in the process is isobutyric acid.

Preferably, the 1-haloalkyl carbonate is CEC-NP.

Optionally, prior to the combining step, the coupling agent is added to a solution of carboxylic acid and a solvent selected from the group consisting of: acetonitrile, C$_3$ to C$_7$ ketones, C$_5$ to C$_{10}$ ethers, C$_2$ to C$_7$ esters, C$_5$ to C$_{10}$ hydrocarbons and a combination thereof. Preferably, the solvent is toluene. Preferably, the process is done at a temperature of about 60° C. to about 110° C., more preferably, at a temperature of about 75° C. Preferably, the process is done for about 1 hour to about 24 hours, more preferably, for about 10 hours. The 1-haloalkyl carbamate or carbonate is preferably added to the reaction mixture comprising the coupling agent, solvent and carboxylic acid.

Typically, during the process, water is formed. Optionally, the water is removed. Preferably, the removal is done by a Dean Stark apparatus or molecular sieves. Preferably, the removal of water is prior to the addition of the 1-haloalkyl carbamate or carbonate.

The process may be done under neat conditions. Preferably, the process comprises: dissolving 1-haloalkyl carbamate or carbonate in carboxylic acid; and adding a coupling agent selected from the group consisting of: Cu(OAc)$_2$, Zn(OAc)$_2$, Cu$_2$O, CuO, CeO$_2$, NiO, ZnO and Cu(O$_2$CCHMe$_2$)$_2$. More preferably, the coupling agent is ZnO. The process under neat conditions is preferably done at a temperature of about 60° C. to about 110° C., more preferably, at about 60° C.

Preferably, the amount of carboxylic acid used is about 50 equivalents to about 80 equivalents relative to the 1-haloalkyl carbamate or carbonate. More preferably, the amount of carboxylic acid used is about 60 equivalents relative to the 1-haloalkyl carbamate or carbonate.

Preferably, the ratio of the coupling agent to 1-haloalkyl carbamate or carbonate is about 0.7 equivalents to about 10 equivalents, more preferably, of about 1 equivalent to about 3 equivalents, most preferably, of about 1 equivalent.

Preferably, the process may be done in the presence of a catalyst. The catalyst may be selected from the group consisting of: NaI, NaBr, tetrabutylammonium bromide ("TBAB"), tetrabutylammonium iodide ("TBAI"), KBr, KI, LiBr and LiI. Preferably, the catalyst is NaBr, NaI or KI. Preferably, the amount of catalyst is about 0.5 equivalents. Preferably, when the 1-haloalkyl carbonate is a 1-chloroalkyl carbonate, the catalyst mentioned above is used. Preferably, where the 1-haloalkylcarbonate is a 1-bromoalkyl, the catalyst is selected from the group consisting of: NaI, KI, and LiI.

The process preferably further comprises an isolation step. Prior to the isolation step, a mixing step is preferably performed. Prior to the isolation step, a cooling step is preferably performed. Preferably, the cooling is to about room temperature. Preferably, the stirring is for about 1 hour to about 16 hours, more preferably, for about 2 hours. Preferably, the isolation is done by evaporation to obtain a residue. The residue may be further recovered. The recovery may be done by dissolving the residue in ethyl acetate, followed by washing with saturated sodium bicarbonate and brine to obtain a two-phase system. The organic layer may be separated, followed by drying it over magnesium sulfate and evaporating it to obtain the final product.

The present invention also encompasses a process for preparing AEC-NP comprising: combining CEC-NP with isobutyric acid in the presence of a coupling agent, preferably, ZnO. The process parameters are the same as those described above.

The present invention encompasses efficient and low cost processes for the preparation of AEC-NP. The process can be performed as a one-pot process, allowing for increased efficiency and application on an industrial scale. The one-pot process allows the use of a single solvent during the entire process, thus avoiding the need to remove or separate the solvent.

The present invention encompasses a one-pot process for preparing diacid acetal skeleton comprising: combining a $C_1$ to $C_{10}$ alcohol or $C_1$ to $C_{10}$ primary amine; a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloalkyl haloformate of the following formula:

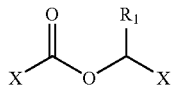

wherein each X is independently selected from Br, I, or Cl and $R_1$ is alkyl or H; and a $C_6$ to $C_{21}$ tertiary amine to obtain a reaction mixture; and adding carboxylic acid to the reaction mixture in the presence of a coupling agent selected from the group consisting of $Cu(OAc)_2$, $Zn(OAc)_2$, $Cu_2O$, $CuO$, $CeO_2$, $NiO$, $ZnO$ and $Cu(O_2CCHMe_2)_2$. Most preferably, the solvent is toluene.

Preferably, the $C_{1-10}$ alcohol has the formula $R_2$—Y—H wherein Y is O, and the $C_{1-10}$ primary amine has the formula $R_2$—$YH_2$ wherein Y is N. Preferably, $R_2$ is alkyl or a substituted aromatic hydrocarbon. More preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', —N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a moiety selected from the group consisting of: —NO$_2$, —S(O)$_2$O—, —S(O)$_2$OH and —S(O)$_2$R', most preferably, $R_2$ is p-nitrophenyl.

Preferably, the 1-haloalkyl carbonate is CEC-NP.

Preferably, the process comprises dissolving $C_1$ to $C_{10}$ alcohol or $C_1$ to $C_{10}$ primary amine in a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof, followed by the addition of 1-haloalkyl haloformate and $C_6$ to $C_{21}$ tertiary amine to obtain a reaction mixture, and adding carboxylic acid to the reaction mixture in the presence of a coupling agent selected from the group consisting of $Cu(OAc)_2$, $Zn(OAc)_2$, $Cu_2O$, $CuO$, $CeO_2$, $NiO$, $ZnO$ and $Cu(O_2CCHMe_2)_2$.

Preferably, the $C_1$ to $C_{10}$ alcohol is a $C_6$ to $C_{10}$ aromatic alcohol, more preferably, phenol, more preferably, a substituted phenol, even more preferably, phenol substituted with a nitro group, most preferably, 4-nitrophenol. Preferably, the $C_1$ to $C_{10}$ primary amine is a $C_6$ to $C_{10}$ primary aromatic amine, more preferably, aniline.

Preferably, the solvent is toluene.

Optionally, the solution of the $C_{1-10}$ alcohol or $C_{1-10}$ primary amine in the solvent is cooled before the addition of the 1-haloalkyl haloformate and $C_6$ to $C_{21}$ tertiary amine. Preferably, the cooling is to a temperature of about 15° C. to about 0° C., more preferably, to a temperature of about 10° C. to about 0° C., most preferably, to a temperature of about 5° C.

Preferably, the $C_6$ to $C_{21}$ tertiary amine is tributyl amine or triethyl amine.

Preferably, $C_6$ to $C_{21}$ tertiary amine is added drop-wise, followed by the addition of 1-haloalkyl haloformate.

Preferably, following the addition of $C_6$ to $C_{21}$ tertiary amine, a stirring step is performed. Preferably, the stirring is for about 30 minutes to about 10 hours. Preferably, the stirring is at a temperature of about 10° C. to about 100° C., more preferably, the stirring is at about room temperature.

Preferably, when the tertiary amine is TBA, prior to the carboxylic acid addition, the reaction mixture is washed with HCl and water. The organic phase is further combined with the carboxylic acid in the presence of the coupling agent, as described above.

Preferably, when the tertiary amine is TEA, prior to the carboxylic acid addition, a filtration step is performed. The obtained filtrate is preferably combined with the carboxylic acid in the presence of the coupling agent, as described above.

Preferably, the coupling agent is ZnO. Preferably, the amount of the coupling agent is about 1 equivalent.

Preferably, the diacid acetal skeleton is AEC-NP.

Preferably, the carboxylic acid used in the process is isobutyric acid.

Preferably, the 1-haloalkyl carbonate is CEC-NP.

Preferably, the addition of the carboxylic acid in the presence of the coupling agent is done at a temperature of about 60° C. to about 110° C., more preferably, at a temperature of about 75° C. Preferably, the addition of the carboxylic acid in the presence of the coupling agent is done for about 1 hour to about 24 hours, more preferably, for about 10 hours.

Preferably, the amount of carboxylic acid used is about 50 equivalents to about 80 equivalents relative to the 1-haloalkyl carbamate or carbonate. More preferably, the amount of carboxylic acid used is about 60 equivalents relative to the 1-haloalkyl carbamate or carbonate.

Preferably, the ratio of the coupling agent to 1-haloalkyl carbamate or carbonate is of about 1 equivalent to about 10 equivalents, more preferably, of about 1 equivalent to about 3 equivalents, most preferably, of about 1 equivalent.

Preferably, the addition of the carboxylic acid in the presence of the coupling agent may be done in the presence of a catalyst. The catalyst is preferably selected from the group consisting of: NaI, NaBr, tetrabutylammonium bromide ("TBAB"), tetrabutylammonium iodide ("TBAI"), KBr, KI, LiBr and LiI. Preferably, the catalyst is NaBr, NaI or KI. Preferably, the amount of catalyst is about 0.5 equivalents.

Preferably, when the 1-haloalkyl carbonate is a 1-chloroalkyl carbonate, the catalyst mentioned above is used. Preferably, where the 1-haloalkylcarbonate is a 1-bromoalkyl, the catalyst is selected from the group consisting of: NaI, KI, and LiI.

The present invention further encompasses a process for preparing AEC-NP comprising: combining 4-nitrophenol with toluene, 1-chloroethyl chloroformate, a base selected from the group consisting of TEA and TBA; and adding isobutyric acid in the presence of a coupling agent, such as ZnO.

The present invention also encompasses a process for preparing GBPE comprising preparing AEC-NP according to the processes described above and further converting it to GBPE.

The present invention encompasses an efficient process for the preparation of gabapentin enacarbil which lowers the amount of gabapentin equivalents used in the process. Preferably, the mole equivalent of gabapentin to the diacid acetal skeleton is less than about 1.9 equivalents, more preferably, about 1 to about 1.9 equivalents, more preferably, about 1 to about 1.5 equivalents.

The present invention further encompasses a process for preparing gabapentin enacarbil comprising: combining gabapentin with a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a base selected from a group consisting of: $C_6$ to $C_{21}$ tertiary amine, $K_2CO_3$, $KHCO_3$, $Na_2CO_3$ and $NaHCO_3$; and AEC-NP.

AEC-NP may be obtained by any method known in the art, preferably, according to the process described in the present invention.

Preferably, the solvent is toluene.

Preferably, the base is $K_2CO_3$ or $Na_2CO_3$.

Preferably, the $C_6$ to $C_{21}$ tertiary amine is TBA or TEA.

Preferably, when the base is $K_2CO_3$, $KHCO_3$, $Na_2CO_3$ or $NaHCO_3$, the base is added with water.

Optionally, when the base is a $C_6$ to $C_{21}$ tertiary amine, prior to the addition of the base, chlorotrimethylsilane may be added.

Preferably, following the addition of the base, a stirring step is performed. Preferably, the stirring is at about 10° C. to about 100° C. Preferably, when the base is a $C_6$ to $C_{21}$ tertiary amine, the stirring is at about room temperature. Preferably, when the base is $K_2CO_3$, $KHCO_3$, $Na_2CO_3$ or $NaHCO_3$, the stirring is at a temperature of about 40° C. to about 60° C.

Preferably, AEC-NP is added with the same solvent used in the process.

Preferably, following the addition of AEC-NP, a stirring step is performed. Preferably, the stirring is for about 2 hours to about 48 hours, more preferably, for about 7 hours. Preferably, the stirring is at a temperature of about 10° C. to about 100° C., more preferably, at about room temperature.

GBPE obtained according to the process above may contain NP and/or NP derivatives. Optionally, the obtained GBPE is GBPE-mix.

Optionally, GBPE is recovered. Preferably, when the base is a $C_6$ to $C_{21}$ tertiary amine, the recovery comprises: washing with HCl and water to obtain a two-phase system; separating the phases; and removing the solvent from the organic phase. Preferably, when the base is $K_2CO_3$, $KHCO_3$, $Na_2CO_3$ or $NaHCO_3$, the recovery comprises: washing with water to obtain a two-phase system; separating the phases, acidifying the aqueous phase with HCl and extracting with toluene.

The present invention provides a purification process of GBPE comprising reducing the NP and NP derivatives in GBPE, followed by acidic extractions. Preferably, the obtained product contains less than about 0.1% area by HPLC, preferably less than about 0.05% area by HPLC, more preferably, no detectable level of NP and/or NP derivatives in GBPE by HPLC. The reduction may be done by either hydrogenating with gaseous $H_2$, by transfer hydrogenation, with formic acid salt or by Single Electron Transfer ("SET"). The acidic extraction may be done with any acid known in the art, preferably, HCl.

In a preferred embodiment, the purification process comprises: combining GBPE containing NP and/or NP derivatives with a polar solvent or an aromatic solvent to obtain a solution, adding gaseous $H_2$ or formic acid salt in the presence of Pd/C or Pt/C to the solution; and extracting with an acid to obtain GBPE.

Preferably, the polar solvent is selected from the group consisting of, MeOH and EtOH.

Preferably, the aromatic solvent is selected from the group consisting of toluene, o-xylene, m-xylene and p-xylene. Most preferably, the solvent is toluene.

Preferably, the formic acid salt is ammonium formate or potassium formate.

Preferably, the formic acid salt is added with water. Preferably, the ratio of the formic acid salt:water (mole:mole) is of about 1:1 to about 1:20, more preferably, of about 1:1 to about 1:10, most preferably, of about 1:3 to 1:6.

Preferably, the gaseous $H_2$ is added at a pressure of about 1 to 6 atmospheres, more preferably, at a pressure of about 3 atmospheres.

Preferably, prior to the extraction, a reaction mixture is obtained. Preferably, the reaction mixture is maintained and further filtered. The maintaining step may be done for about 2 hours to about 24 hours, more preferably, for about 2 hours to about 12 hours. Preferably, the maintaining step is done with stirring. Preferably, when $H_2$ gaseous is used in the process, the stirring is at about room temperature to about 60° C., more preferably, at about room temperature. Preferably, when formic acid salt is used in the process, the stirring is at about room temperature to about 60° C., more preferably, at about 45° C.

Prior to the extraction step, the reaction mixture may be filtered and optionally further dried. The drying may be done by evaporation.

The acidic extraction may be done by adding HCl and brine, optionally with water, to obtain a two phase system; separating the phases and removing the solvent from the organic phase. Preferably, the solvent is removed by evaporation.

When the polar solvent is MeOH or EtOH, prior to the washing step, the solvent is preferably removed to obtain a residue, and toluene is preferably added to obtain a solution.

In another embodiment, the purification process is a Single Electron Transfer ("SET") process comprising: dissolving GBPE containing NP and/or NP derivatives in $C_1$-$C_4$ carboxylic acid or HCl to obtain a solution; adding a metal selected from the group consisting of: iron, zinc and magnesium to the solution; and extracting with acid.

Preferably, the $C_1$-$C_4$ carboxylic acid is acetic acid.

Preferably, the metal is iron. Preferably, the iron is powdery.

Preferably, prior to the extraction step, a reaction mixture is obtained. The reaction mixture may be stirred, preferably at a temperature of about 10° C. to about 100° C., more preferably, at about 45° C. The stirring may be done for about 1 hour to about 24 hours, more preferably, for about 2.5 hours. Following the stirring step, the reaction mixture is cooled. The cooling may be done to about room temperature.

The extraction may be done by adding water and toluene to obtain a two phase system; separating the phases; washing the organic phase with HCl, water and brine; drying the organic phase; and removing the solvent. The drying may be done over sodium sulfate. The removal of the solvent may be done by evaporation. The evaporation may be done at reduced pressure.

The product obtained from the purification process above is preferably pure from NP and its derivatives.

The present invention provides another purification process of GBPE comprising loading GBPE on a column filled with cross-linked dextran gel (e.g., Sephadex LH-20, which is reported to have a bead size of about 25-100 microns, or other similar resin) in toluene; and eluting GBPE with toluene or a toluene/hexane solution to obtain GBPE. Preferably, the cross-linked dextran gel is cross-linked dextran gel having a bead size about the same as Sephadex LH-20. Preferably, the obtained product contains less than about 0.1% area by HPLC, preferably less than about 0.05% area by HPLC, more preferably, no detectable level of NP and/or NP derivatives in GBPE by HPLC.

Preferably, when a toluene/hexane solution is used, the ratio of the toluene to hexane is about 1:1 to about 10:1, more preferably, about 4:1.

Optionally, the above purification process may be repeated.

The present invention further encompasses a one-pot reaction for the preparation of GBPE. In preferred embodiments this process is efficient, time saving, and results in a higher yield than that of the prior art. The process may be illustrated according to the scheme below.

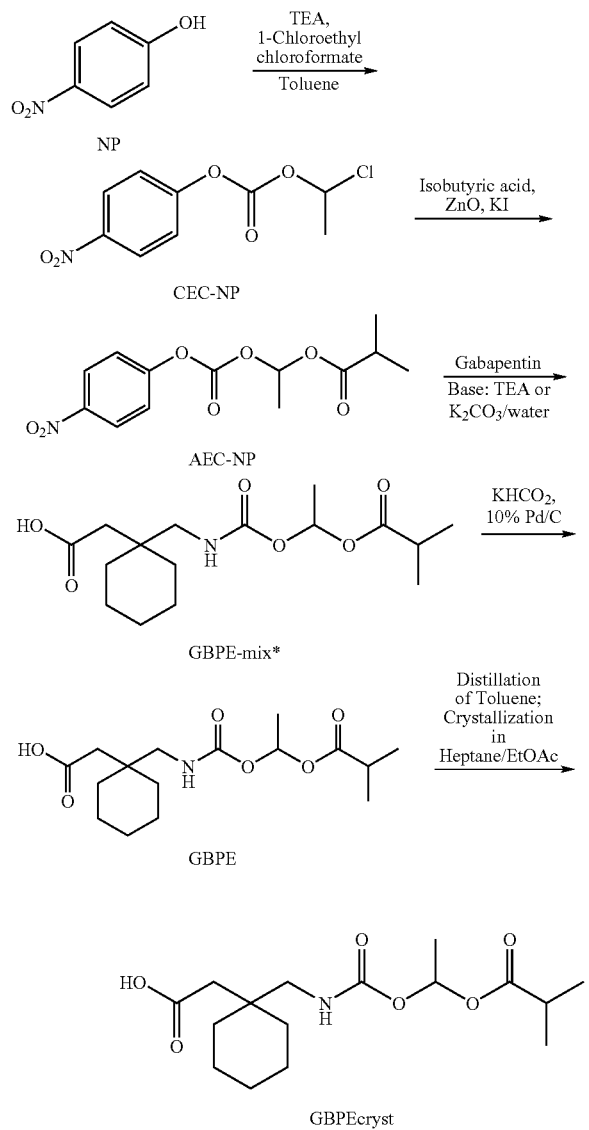

The present invention encompasses a one-pot process for preparing GBPE comprising: combining $C_1$ to $C_{10}$ alcohol or $C_1$ to $C_{10}$ primary amine; a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof; a 1-haloethyl haloformate of the following formula:

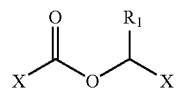

wherein X is independently selected from Br, I, or Cl and $R_1$ is methyl; and a $C_6$ to $C_{21}$ tertiary amine; adding isobutyric acid in the presence of a coupling agent selected from the group consisting of $Cu(OAc)_2$, $Cd(OAc)_2$, $Zn(OAc)_2$, $Cu_2O$, CuO, $CeO_2$, CdO, NiO, ZnO and $Cu(O_2CCHMe_2)_2$; adding gabapentin and a base selected from a group consisting of: $C_6$ to $C_{21}$ tertiary amine, $K_2CO_3$, $KHCO_3$, $Na_2CO_3$ and $NaHCO_3$ to obtain GBPE; reducing the GBPE, followed by acidic extraction, concentrating the solvent and adding hexane, heptane or a solution of heptane and EtOAc to obtain a precipitate.

Preferably, the $C_{1-10}$ alcohol has the formula $R_2$—Y—H wherein Y is O, and the $C_{1-10}$ primary amine has the formula $R_2$—$YH_2$ wherein Y is N. Preferably, $R_2$ is alkyl or a substituted aromatic hydrocarbon. More preferably, $R_2$ is alkyl or a substituted aromatic hydrocarbon mono-substituted at ortho- or para-positions with a moiety selected from the group consisting of: halo, —C(halo)$_3$, —CF$_3$, —CN, —OCN, —SCN, —N$_3$, —NO$_2$, —S(O)$_2$O—, —S(O)$_2$OH, —S(O)$_2$R', —OS(O$_2$)O—, —OS(O)$_2$R', —OP(O)(OR'), —C(O)R', —C(S)R', —C(O)OR', —C(O)NR'R", —C(O)O—, —C(S)OR', _N(R)C(O)NR'R", —N(R)C(S)NR'R", —N(R)C(NR')N(R)'R" and —C(NR')NR'R, wherein each R, R' and R" are independently selected from the group consisting of: hydrogen and alkyl. Optionally, R, R' and R", together with the atom to which they are attached, form a cycloheteroalkyl or substituted cycloheteroalkyl ring. More preferably, $R_2$ is a substituted aromatic hydrocarbon substituted with a moiety selected from the group consisting of: —NO$_2$, —S(O)$_2$O—, —S(O)$_2$OH and —S(O)$_2$R', most preferably, $R_2$ is p-nitrophenyl.

Preferably, the process comprises dissolving $C_1$ to $C_{10}$ alcohol or $C_1$ to $C_{10}$ primary amine and $C_6$ to $C_{21}$ tertiary amine in a solvent selected from the group consisting of: acetonitrile, $C_3$ to $C_7$ ketone, $C_5$ to $C_{10}$ ether, $C_2$ to $C_7$ ester, $C_5$ to $C_{10}$ hydrocarbon and a combination thereof, followed by the addition of 1-haloalkyl haloformate to obtain a reaction mixture, and adding carboxylic acid to the reaction mixture in the presence of a coupling agent selected from the group consisting of $Cu(OAc)_2$, $Zn(OAc)_2$, $Cu_2O$, CuO, $CeO_2$, NiO, ZnO and $Cu(O_2CCHMe_2)_2$, adding GBP, and a base selected from a group consisting of: $C_6$ to $C_{21}$ tertiary amine, $K_2CO_3$, $KHCO_3$, $Na_2CO_3$ and $NaHCO_3$ to obtain GBPE; reducing the obtained GBPE, followed by acidic extraction, concentrating the solvent and adding hexane, heptane or a solution of heptane and EtOAc to obtain a precipitate.

Preferably, the $C_6$ to $C_{21}$ tertiary amine is a $C_6$ to $C_{12}$ tertiary amine More preferably, the $C_6$ to $C_{21}$ tertiary amine is a TEA.

Typically, the $C_1$ to $C_{10}$ alcohol is a $C_6$ to $C_{10}$ aromatic alcohol, more preferably, phenol, more preferably, a substituted phenol, even more preferably, phenol substituted with a nitro group, most preferably, 4-nitrophenol. Preferably, the $C_1$ to $C_{10}$ primary amine is a $C_6$ to $C_{10}$ primary aromatic amine, more preferably, aniline.

Preferably, the solvent is toluene.

Optionally, prior to the addition of 1-haloethyl haloformate the solution is cooled. Preferably, the cooling is to a temperature of about 15° C. to about 0° C., more preferably, to a temperature of about 10° C. to about 0° C., most preferably, to a temperature of about 5° C.

Preferably, the 1-haloethyl haloformate is 1-chloroethyl chloroformate.

Preferably, the $C_6$ to $C_{21}$ tertiary amine is tributyl amine or triethyl amine Preferably, the 1-haloethyl haloformate is added dropwise.

Preferably, following the addition of $C_6$ to $C_{21}$ tertiary amine, a stirring step is performed. Preferably, the stirring is at a temperature of about 10° C. to about 100° C., more preferably, the stirring is at about room temperature.

Preferably, when the tertiary amine is TEA, prior to the carboxylic acid addition, a filtration step is performed. The obtained filtrate is preferably combined with the carboxylic acid in the presence of the coupling agent, as described above.

Preferably, the coupling agent is ZnO. Preferably, the amount of the coupling agent is about 1 equivalent.

Preferably, the addition of the carboxylic acid in the presence of the coupling agent may be done in the presence of a catalyst. The catalyst may be selected from the group consisting of: NaI, NaBr, tetrabutylammonium bromide ("TBAB"), tetrabutylammonium iodide ("TBAI"), KBr, KI, LiBr and LiI. Preferably, the catalyst is NaBr, NaI or KI. Preferably, the amount of catalyst is about 0.5 equivalents.

Optionally, following the addition of carboxylic acid in the presence of the coupling agent, a heating step is performed, followed by a cooling step. Preferably, the heating is to a temperature of about 60° C. to about 100° C., more preferably, about 80° C. Preferably, the cooling is to about room temperature. Preferably, following the cooling step, water is added to obtain a two-phase system, the phases are separated, and the organic phase is further washed with aqueous Na2CO3 to obtain a pH of about 6 to about 7 in a two-phase system. The two-phase system is further separated and the organic phase is kept for the next step where GBP is added.

Preferably, the carboxylic acid used in the process is isobutyric acid.

Preferably, the base selected from a group consisting of: $C_6$ to $C_{21}$ tertiary amine, $K_2CO_3$, $KHCO_3$, $Na_2CO_3$ and $NaHCO_3$ is $K_2CO_3$ or $Na_2CO_3$.

Preferably, the $C_6$ to $C_{21}$ tertiary amine is TBA or TEA.

Preferably, when the base is $K_2CO_3$, $KHCO_3$, $Na_2CO_3$ or $NaHCO_3$, the base is added with water.

Preferably, following the addition of GBP and the base, a stirring step is performed. Preferably, the stirring is at about 10° C. to about 100° C. Preferably, when the base is a $C_6$ to $C_{21}$ tertiary amine, the stirring is at about room temperature.

Preferably, the reduction is done by hydrogenation, transfer hydrogenation or SET.

In a preferred embodiment, the reduction process comprises: adding gaseous $H_2$ or formic acid salt in the presence of Pd/C or Pt/C to the solution; and extracting with an acid to obtain GBPE.

Preferably, the formic acid salt is added with water. Preferably, the ratio of the formic acid salt:water (mole:mole) is of about 1:1 to about 1:20, more preferably, of about 1:1 to about 1:10, most preferably, of about 1:3 to 1:6.

Preferably, the gaseous $H_2$ is added at a pressure of about 1 to 6 atmospheres, more preferably, at a pressure of about 3 atmospheres.

Preferably, prior to the extraction, a reaction mixture is obtained. Preferably, the reaction mixture is maintained and further filtered. The maintaining step may be done for about 2 hours to about 24 hours, more preferably, for about 2 hours to about 12 hours. Preferably, the maintaining step is done with stirring. Preferably, when $H_2$ gaseous is used in the process, the stirring is at about room temperature to about 60° C., more preferably, at about room temperature. Preferably, when formic acid salt is used in the process, the stirring is at about room temperature to about 60° C., more preferably, at about 45° C.

Alternatively, the reduction process is a Single Electron Transfer ("SET") process comprising: adding a metal selected from the group consisting of: iron, zinc and magnesium; and extracting with acid.

Preferably, the metal is iron. Preferably, the iron is powdery.

Prior to the extraction step, the reaction mixture may be filtered and optionally further dried. The drying may be done by evaporation.

Optionally, the acidic extraction is done by adding HCl and brine, optionally with water, to obtain a two phase system; separating the phases and removing the solvent from the organic phase. Preferably, the solvent is removed by evaporation.

When the polar solvent is MeOH or EtOH, prior to the washing step, the solvent is preferably removed to obtain a residue, and toluene is preferably added to obtain a solution.

Preferably, prior to the extraction step, a reaction mixture is obtained. The reaction mixture may be stirred, preferably at a temperature of about 10° C. to about 100° C., more preferably, at about 45° C. The stirring may be done for about 1 hour to about 24 hours, more preferably, for about 2.5 hours. Following the stirring step, the reaction mixture is cooled. The cooling may be done to about room temperature.

The extraction may be done by adding water and toluene to obtain a two phase system; separating the phases; washing the organic phase with HCl, water and brine; drying the organic phase; and removing the solvent. The drying may be done over sodium sulfate. The removal of the solvent may be done by evaporation. The evaporation may be done at reduced pressure.

The product obtained from the purification process above is preferably pure from NP and its derivatives.

The concentration may be done by vacuum distillation. As used herein, the term "vacuum distillation" refers to a distillation step under vacuum, at a temperature of about 50° C. to about 80° C., more preferably, of about 50° C. to about 60° C.

Preferably, following the addition of hexane, heptane or heptane/EtOAc solution, a cooling step is performed. Preferably, the cooling is to a temperature of about room temperature to about 0° C., more preferably, to about 5° C., to allow precipitation.

The present invention further encompasses a one-pot process for preparing GBPE comprising: combining 4-nitrophenol, toluene, 1-chloroethyl chloroformate and a base selected from the group consisting of TEA and TBA; adding isobutyric acid in the presence of ZnO; adding GBP and a base selected from the group consisting of TEA and $K_2CO_3$; adding potassium formate in the presence of palladium over carbon; and adding hexane, heptane or heptane/EtOAc.

Having thus described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to, limit its scope in any way. Absent statement to the contrary, any combination of the specific embodiments described above are consistent with and encompassed by the present invention.

INSTRUMENTS

Water Removing Tool:
  Molecular sieves, Dean Stark apparatus.
HPLC

| Column & Packing: | Zorbax sb phenyl 100 * 4.6 1.8μ | | |
|---|---|---|---|
| Eluent A: | A: 0.025% H2SO4 in water | | |
| Eluent B: | B: Acetonitrile | | |
| | Time | % Eluent A | % Eluent B |
| Gradient | 0 | 70 | 30 |
| | 5 | 70 | 30 |
| | 20 | 60 | 40 |
| | 45 | 10 | 90 |
| Equilibrium time: | 8 min | | |
| Flow: | 1.0 ml/min | | |
| Sample volume: | 10 μL | | |
| Detector: | 210 nm | | |
| Column temperature: | 25° C. | | |
| Diluent | Water:ACN (50:50) | | |

Sample Preparation

Weigh accurately about 40 mg of sample in a 20 ml volumetric flask. Dissolve with diluent.

Method

Inject the sample solutions into the chromatograph, continuing the chromatogram of sample up to the end of the gradient. Determine the areas for each peak in each solution using a suitable integrator.

EXAMPLES

Example 1

Preparation of CEC-NP

Reactor (500 ml) was loaded with 4-Nitrophenol (10 g, 0.07 mol) dissolved in Toluene (150 ml) followed by dropwise addition of 1-chloroethyl chloroformate (13.25 g, 0.09 mol) and then Tributyl amine (17.3 g, 0.09 mol). The obtained solution was stirred at room temperature for additional 30 min. At this point according to HPLC no 4-Nitrophenol remained. The reaction was washed with 1N HCl (150 ml), water (2*100 ml) and brine. The aqueous phase was removed from the reactor and to the remaining toluenic solution was evaporated.

Example 2

One-Pot Process for Preparation of AEC-NP

Reactor (500 ml) was loaded with 4-Nitrophenol (10 g, 0.07 mol) dissolved in Toluene (150 ml) followed by dropwise addition of 1-chloroethyl chloroformate (13.25 g, 0.09 mol) and then Tributyl amine (17.3 g, 0.09 mol). The obtained solution was stirred at room temperature for additional 30 min. At this point according to HPLC no 4-Nitrophenol remained. The reaction was washed with 1N HCl (150 ml), water (2*100 ml) and brine. The aqueous phase was removed from the reactor and to the remained toluenic solution was added Zinc oxide (17 g, 0.21 mol), Sodium iodide (10.5 g, 0.07 mol) and Isobutyric acid (50 ml). The obtained mixture was heated at 75° C. monitored by HPLC. The reaction was stopped approximately after 10 h. The reaction was washed with NaHCO₃ solution and then with brine. The solvent was evaporated to give the product in 60% yield.

Example 3

One-Pot Process for Preparation of AEC-NP

Reactor was loaded with 4-Nitrophenol (5 g, 35 mmol) dissolved in Toluene (75 ml) followed by addition of triethylamine (TEA) (3.8 g, 38.5 mmol). The obtained yellow colored solution was cooled to 5° C. and then 1-chloroethyl chloroformate (38.5 mmol) was added dropwise. The obtained jelly-like slurry was stirred for additional 30 min, at this point according to HPLC no 4-Nitrophenol remained. The reaction mixture was filtered; the filtrate was loaded to the reactor followed by addition of Zinc oxide (38.5 mmol), Potassium iodide (19.3 mmol) and Isobutyric acid (43 ml). The obtained mixture was heated at 80° C. monitored by HPLC. The reaction was stopped approximately after 10 h. The reaction was washed with NaHCO₃ solution, 20% Na₂S₂O₃ solution and then with brine. The solvent was evaporated to give the product in 40% to 50% yield.

Example 4

Preparation of AEC-NP from CEC-NP 1-1-chloroethyl 4-nitrophenyl carbonate [CEC-NP] (1 g, 4 mmol) was dissolved in isobutyric acid (20 ml) followed by addition of zinc oxide (1 g, 12 mmol) and NaBr (0.41 g, 4 mmol). The reaction mixture was stirred at 60° C. for 24 hours. The reaction was stopped and evaporated; the residue was dissolved in EtOAc, washed with saturated NaHCO₃ solution and then with brine. The organic layer was separated, dried over MgSO₄ and evaporated to give the desired product in 60% yield.

Example 5

Preparation of AEC-NP from CEC-NP

Zinc oxide (1 g, 12 mmol) was added to a solution of toluene (40 ml) and isobutyric acid (10 ml) and the flask was heated at 105° C. The water created in this process was removed by Dean Stark apparatus. After 1 h of heating, the temperature was lowered to 60° C. and then 1-1-chloroethyl 4-nitrophenyl carbonate [CEC-NP] (1 g, 4 mmol) together with NaI (1 g, 6.4 mmol) were added. The reaction mixture was stirred at 60° C. for 24 hours. The reaction was stopped and evaporated; the residue was dissolved in EtOAc, washed with saturated NaHCO₃ solution and then with brine. The organic layer was separated, dried over MgSO₄ and evaporated to give the desired product in 75% yield.

Example 6

Preparation of GBPE from AEC-NP

Gabapentin free base (5.75 g, 0.03 mol) was slurried in Toluene (50 ml) followed by addition of chlorotrimethylsilane (6.5 g, 0.06 mol) and Tributyl amine (11.1 g, 0.06 mol). The resulting mixture was stirred at room temperature to give clear solution. Then 1-(isobutyryloxy)ethyl 4-nitrophenyl carbonate [AEC-NP] (10 g, 0.03 mol) in Toluene (20 ml) was added and the reaction was stirred at RT for 24 h. The reaction was washed with 1N HCl (150 ml) and hot water (5*100 ml). The toluenic phase was washed with saturated NaHCO₃ and the phases were separated. The aqueous phase was acidified with 1N HCl and extracted with Toluene. The last toluenic phase was dried and evaporated to give GBPE.

Example 7

Preparation of GBPE from AEC-NP

Gabapentin free base (5.75 g, 0.03 mol) was slurried in Toluene (50 ml) followed by addition of Chlorotrimethylsilane (6.5 g, 0.06 mol) and Tributyl amine (11.1 g, 0.06 mol). The resulting mixture was stirred at room temperature to give clear solution. Then 1-(isobutyryloxy)ethyl 4-nitrophenyl carbonate [AEC-NP] (10 g, 0.03 mol) in Toluene (20 ml) was added and the reaction was stirred at RT for 24 h. The reaction was washed with 1N HCl (150 ml) and water (2*100 ml). The toluenic phase was dried and evaporated to give GBPE in quantitative yield.

Purification of GBPE from NP and its Derivatives
Method A: Hydrogenation:

Example 8

In Toluene (I)

GBPE crude (3.5 g) was dissolved in toluene followed by addition of 10% Pd/C (20% wt) and the obtained mixture was hydrogenated at 3 atm for 2 h to 24 h. Then the reaction was filtered, the filtrate was washed with 1N HCl, brine and the organic phase was evaporated to give GBPE pure from nitrophenol derived impurities.

Example 9

In MeOH (I)

GBPE crude (3.5 g) was dissolved in MeOH followed by addition of 10% Pd/C (20% wt) and the obtained mixture was hydrogenated at 3 atm for 2 h to 24 h. Then the reaction was filtered, and the filtrate was evaporated. The residue was dissolved in toluene and washed with 1N HCl, brine and the organic phase was evaporated to give GBPE pure from nitrophenol derived impurities.

Example 10

In EtOH (I)

GBPE crude (3.5 g) was dissolved in EtOH followed by addition of 10% Pd/C (20% wt) and the obtained mixture was hydrogenated at 3 atm for 2 h to 24 h. Then the reaction was filtered, and the filtrate was evaporated. The residue was dissolved in toluene and washed with 1N HCl, brine and the organic phase was evaporated to give GBPE pure from nitrophenol derived impurities.

Method B: Transfer Hydrogenation:

Example 11

In Toluene (II)

GBPE crude (3.5 g) was dissolved in toluene followed by addition of 10% Pd/C (20% wt) and Ammonium formate (1 eq). The resulting reaction mixture was stirred at RT for 2 h to 24 h. Then the reaction was filtered, the filtrate was washed with 1N HCl, brine and the organic phase was evaporated to give GBPE pure from nitrophenol derived impurities.

Example 12

In MeOH (II)

GBPE crude (3.5 g) was dissolved in MeOH followed by addition of 10% Pd/C (20% wt) and Ammonium formate (1 eq). The resulting reaction mixture was stirred at RT for 2 h to 24 h. Then the reaction was filtered, and the filtrate was evaporated. The residue was dissolved in toluene and washed with 1N HCl, brine and the organic phase was evaporated to give GBPE pure from nitrophenol derived impurities.

Example 13

In EtOH (II)

GBPE crude (3.5 g) was dissolved in EtOH followed by addition of 10% Pd/C (20% wt) and Ammonium formate (1 eq). The resulting reaction mixture was stirred at RT for 2 h to 24 h. Then the reaction was filtered, and the filtrate was evaporated. The residue was dissolved in toluene and washed with 1N HCl, brine and the organic phase was evaporated to give GBPE pure from nitrophenol derived impurities.

Method C: Single Electron Transfer:

Example 14

GBPE crude (0.5 g) (containing nitrophenol (8%) and derivatives of nitrophenol (about 10%)) was dissolved in acetic acid (6 mL). Iron powder (0.5 g) was added and the mixture was stirred at 45° C. for 2.5 hours. TLC (Hexane/EtOAc, 1:2) indicated full consumption of nitrophenol. The mixture was cooled to 25° C. and diluted with water. GBPE was extracted by toluene. The toluene solution was consequently washed with HCl (1N), water and brine, dried over sodium sulfate. The solvent was removed at reduced pressure, giving the product (0.29 g) as viscous oil.

Method D: Filtration on Sephadex LH-20

Example 15

GBPE crude (1 g) containing 20% of Nitrophenol (NP) was loaded on column filed with Sephadex LH-20 in Toluene (40 g of stationary phase). GBPE was eluted with Toluene/Hexane (4:1) solution monitored by TLC. Fractions containing GBPE were combined together and evaporated to dryness to give GBPE and 0.27% of NP. The recovery of GBPE was 97.7%. This experiment can be repeated in order to achieve GBPE fraction which contains undetectable levels of NP.

One-Pot Process for Preparation of GBPE from NP

Example 16

Method A

Stage 1: 4-Nitrophenol (50 g, 0.36 mol) and Triethylamine [TEA] (42 g, 0.415 mol, 1.15 eq) were dissolved in Toluene (750 ml, 15V) and the obtained reaction mixture was cooled at 5° C. under $N_2$. 1-chloroethyl-chloroformate (59.5 g, 0.415 mol, 1.15 eq) was added dropwise and then the reaction is allowed to reach room temperature. The reaction progress was monitored by HPLC, no 4-Nitrophenol was detected after 1 h. The reaction was filtered, the cake was washed with Toluene (2*100 ml) and the filtrate was returned to the reactor.

Stage 2: Zinc oxide (30 g, 0.36 mol), Potassium iodide (30 g, 0.18 mol) and Isobutyric acid (400 ml) were loaded into the reactor and the reaction mixture was heated at 80° C. approximately for 8 h. Then the reactor was cooled to RT and the reaction was washed with water (500 ml). After phase separation additional amount of water (1 L) was added and the pH was adjusted to 6.5-7 by portionwise addition of solid NaHCO$_3$. The organic phase was washed with 20% Na$_2$S$_2$O$_3$ (1 L) and with water (2*1 L). After phase separation, assay percentage of the desired intermediate in the solution was measured.

Stage 3: To the toluenic phase were added Gabapentin (42.91 g, 0.25 mol [1.5 eq vs AEC-NP]) and Triethylamine [TEA] (25.38 g, 0.25 mol [1.5 eq vs. AEC-NP]) and the reaction was heated at 40° C. The reaction progress was monitored by HPLC, when no AEC-NP was detected (approximately after 7 h) the reaction was cooled to RT and the solution was washed with 1N HCl (1 L). The phases were separated and the toluenic phase was washed with water (1 L).

Stage 4: To the toluenic phase were added Potassium formate (45 g, 0.53 mol [1.5 eq vs. NP]) and 10% Pd/C (50% water content, 15 g). The reaction was heated at 45° C. and was monitored by HPLC. The reaction was stopped when no 4-Nitrophenol was detected. The reaction was filtered on Hyflo bed, washed with Toluene (2*100 ml) and the filtrate was washed with 1N HCl (1 L) and then with water (1 L). The yield until this stage was 40% vs. 4-Nitrophenol (NP) based on assay calculations.

Precipitation stage: The toluenic phase was concentrated by vacuum distillation (50-60° C.) to approximately 1-2V of Toluene (vs. GBPE) followed by addition of Heptane (20-30 V) and cooling to RT to form precipitate which was collected by filtration.

Example 17

Method B

Stage 1: 4-Nitrophenol (50 g, 0.36 mol) and Triethylamine [TEA] (42 g, 0.415 mol, 1.15 eq) were dissolved in Toluene (750 ml, 15V) and the obtained reaction mixture was cooled at 5° C. under N2. Chloroethyl-chloroformate (59.5 g, 0.415 mol, 1.15 eq) was added dropwise and then the reaction was allowed to reach room temperature. The reaction progress was monitored by HPLC, no 4-Nitrophenol was detected after 1 h. The reaction was filtered, the cake was washed with Toluene (2*100 ml) and the filtrate was returned to the reactor.

Stage 2: Zinc oxide (30 g, 0.36 mol), Potassium iodide (30 g, 0.18 mol) and Isobutyric acid (400 ml) were loaded into the reactor and the reaction mixture was heated at 80° C. approximately for 8 h. Then the reactor was cooled to RT and the reaction was washed with water (500 ml). After phase separation the toluenic phase was cooled to 0° C. followed by dropwise addition of 18% Na2CO3 aqueous solution till the pH reached 6.5-7. The phases were separated and the organic phase was washed with 20% Na2S2O3 (500 L) and with water (2*500 L). After phase separation, assay percentage of the desired intermediate in the solution was measured.

Stage 3: To solution of K$_2$CO$_3$ (53.6 g, 0.38 mol [2 eq vs. AEC-NP]) in water (250 ml [5V vs. GBP]) was added Gabapentin (50 g, 0.29 mol [1.5 eq vs AEC-NP]) and the toluenic solution from the previous stage. The obtained reaction mixture was stirred at 40° C. and was monitored by HPLC. When no AEC-NP was detected (approximately after 10 h) the reaction was cooled to RT and water (500 ml) was added. The phases were separated and the aqueous phase was acidified with 2N HCl and extracted with Toluene (1 L). Toluenic phase was stirred at −10° C. for 24 h and then filtered on HiFlo bed.

Stage 4: To the solution of KHCO$_2$ (46 g, 0.54 mol [1.5 eq vs. NP]) in water (29 ml, 1.62 mol [3 eq vs. KHCO$_2$] were added 10% Pd/C (50% water content, 5 g) and the toluenic solution from the previous stage. The reaction was heated at 45° C. and was monitored by HPLC. The reaction was stopped when no 4-Nitrophenol was detected. The reaction was cooled to RT and acidified with 2N HCl (500 ml) followed by filtration on Hyflo bed. The cake was washed with Toluene (2*100 ml) and water (2*100 ml). The phases were separated and organic phase was washed with water (1 L). Toluenic phase was stirred at −10° C. for 24 h and then filtered on HiFlo bed. After filtration the assay of GBPE in the solution was measured. To the toluenic solution was added Na2CO3 aqueous solution [5% molar vs. GBPE] and the biphasic mixture was stirred at RT for 24 h. Then the phases were separated, the organic phase was washed with 1N HCl and then with water. Phases were separated and the yield until this stage was 36% vs. 4-Nitrophenol (NP) based on assay calculations.

Crystallization stage: The toluenic phase was concentrated by vacuum distillation (50-60° C.) to approximately 1-2 Volumes of Toluene (vs. GBPE) followed by addition of Heptane/EtOAc=10:1 (5 V). The crystallization mixture was heated up to 80° C. to give clear solution and then slowly cooled to 40° C. and seeded. The reaction was further slowly cooled to 5° C. The reaction was kept at this temperature for 12 h and the obtained precipitate was collected by filtration.

What is claimed is:

1. A process for purifying gabapentin enacarbil (GBPE) from a mixture with nitrophenol (NP) and/or NP derivatives comprising reducing the NP and NP derivatives in the mixture, followed by acidic extraction.

2. The process of claim 1, wherein the obtained product contains less than about 0.1% area by HPLC of nitrophenol and less than about 0.1% area by HPLC of any nitrophenol derivative.

3. The process of claim 1, wherein the obtained product contains less than about 0.05% area by HPLC of nitrophenol and less than about 0.05% area by HPLC of any nitrophenol derivative.

4. The process of claim 1, wherein the obtained product contains no detectable amount, by area HPLC, of nitrophenol or any nitrophenol derivative.

5. The process of claim 1, wherein the reduction is done by hydrogenating with gaseous H$_2$, by transfer hydrogenation with formic acid salt or by Single Electron Transfer ("SET").

6. The process of claim 1, comprising: combining a mixture containing gabapentin enacarbil, NP, and/or NP derivatives with a polar solvent or an aromatic solvent to obtain a solution, adding gaseous H$_2$ or formic acid salt in the presence of Pd/C or Pt/C to the solution; and extracting with an acid.

7. The process of claim 6, wherein the polar solvent is selected from the group consisting of MeOH and EtOH.

8. The process of claim 6, wherein the aromatic solvent is selected from the group consisting of: toluene, o-xylene, m-xylene and p-xylene.

9. The process of claim 8, wherein the aromatic solvent is toluene.

10. The process of claim 6, wherein the formic acid salt is ammonium formate or potassium formate.

11. The process of claim 6, wherein the formic acid salt is added with water.

12. The process of claim 11, wherein the ratio of the formic acid salt:water (mole:mole) is of about 1:1 to about 1:20.

13. The process of claim 6, wherein the gaseous H$_2$ is added at a pressure of about 1 to about 6 atmospheres.

14. The process of claim 1, comprising dissolving a mixture containing gabapentin enacarbil, nitrophenol, and/or nitrophenol derivatives in a $C_1$-$C_4$ carboxylic acid or HCl to obtain a solution; adding a metal selected from the group consisting of: iron, zinc and magnesium to the solution; and extracting with acid to obtain gabapentin enacarbil.

15. The process of claim 14, wherein the $C_1$-$C_4$ carboxylic acid is acetic acid.

16. The process of claim 14, wherein the metal is iron.

17. A process for purifying gabapentin enacarbil, comprising: loading a mixture containing gabapentin enacarbil, nitrophenol, and/or nitrophenol derivatives on a column filled with cross-linked dextran gel in toluene; and eluting purified gabapentin enacarbil with toluene or a toluene/hexane solution.

18. The process of claim 17, wherein the cross-linked dextran has a bead size of approximately 25-100 microns.

19. The process of claim 17, wherein, when a toluene/hexane solution is used, the ratio of the toluene to hexane is about 1:1 to about 10:1.

20. The process of claim 19, wherein the ratio of the toluene to hexane is about 4:1.

\* \* \* \* \*